United States Patent
Baumgardner et al.

(10) Patent No.: US 7,087,436 B2
(45) Date of Patent: Aug. 8, 2006

(54) MEMBRANE COUNTERCURRENT EXCHANGER AND MEMBRANE INLET MASS SPECTROMETER FOR THE ANALYSIS OF GAS PARTIAL PRESSURE IN LIQUID SAMPLES

(75) Inventors: James Baumgardner, Milmont Park, PA (US); Gordon Neufeld, Flourtown, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/465,637

(22) Filed: Jun. 20, 2003

(65) Prior Publication Data

US 2003/0211629 A1 Nov. 13, 2003

Related U.S. Application Data

(63) Continuation of application No. 08/928,099, filed on Sep. 12, 1997, now abandoned.

(60) Provisional application No. 60/026,035, filed on Sep. 13, 1996.

(51) Int. Cl.
G01N 33/00 (2006.01)
H01J 49/04 (2006.01)

(52) U.S. Cl. .................. 436/173; 73/19.05; 250/281; 250/288; 436/52; 436/68; 436/133; 436/136; 436/138; 436/139; 436/174; 436/178; 436/181

(58) Field of Classification Search .................. 436/52, 436/68, 133, 136, 138–139, 173–174, 178, 436/181; 73/19.05; 250/288, 281–282
See application file for complete search history.

(56) References Cited

U.S. PATENT DOCUMENTS 3,352,422 A * 11/1967 Heden .................... 210/321.67
3,649,199 A * 3/1972 Littlejohn .................... 436/178

(Continued)

FOREIGN PATENT DOCUMENTS

ES 2026358 4/1992

(Continued)

OTHER PUBLICATIONS

Tsao, M. U. et al, J. Clin. Lab Med. 1964, 63, 1041-1053.*

(Continued)

Primary Examiner—Arlen Soderquist
(74) Attorney, Agent, or Firm—Womble Carlyle

(57) ABSTRACT

A method and apparatus for the analysis of blood or other liquids by mass spectrometry to determine the partial pressures of gases and other volatile substances dissolved in the blood or other liquid in a manner independent of the solubility of the gases in the blood or other liquid. A countercurrent membrane exchanger (CCME) is provided for equilibrating a carrier fluid with the sample of blood or other liquid, the output of which is coupled to a tubular direct insertion membrane probe (t-DIMP) type of membrane inlet mass spectrometer. The CCME preferably has complementary spiral grooves on opposing metal plates for the water carrier and sample liquids so as to induce secondary flows which greatly reduce the resistance to equilibration between the liquid sample and water carrier phases. The t-DIMP is characterized by the use of Teflon™ sleeves specifically to reduce noise introduced at the connection between the silicone membrane in the t-DIMP and the steel tubing for the water carrier, by the use of radiation shields to prevent heating of the silicone membrane and water carrier to allow lower carrier flow rates, and by the heating of the section between the ion source and the vacuum pumps specifically to improve linearity of the t-DIMP.

21 Claims, 6 Drawing Sheets

U.S. PATENT DOCUMENTS

| | | | | |
|---|---|---|---|---|
| 3,712,111 | A | * | 1/1973 | Llewellyn .................. 73/23.37 |
| 3,929,003 | A | | 12/1975 | Llewellyn .................. 73/61.72 |
| 4,005,700 | A | * | 2/1977 | Parker ......................... 600/364 |
| 4,016,864 | A | * | 4/1977 | Sielaff et al. ............... 600/364 |
| 4,110,220 | A | | 8/1978 | Lavender ............... 210/321.75 |
| 4,209,299 | A | | 6/1980 | Carlson ....................... 436/150 |
| 4,268,279 | A | * | 5/1981 | Shindo et al. .................. 95/46 |
| 4,388,531 | A | * | 6/1983 | Stafford et al. ............. 250/427 |
| 4,516,580 | A | * | 5/1985 | Polanyi ....................... 600/364 |
| 4,791,292 | A | * | 12/1988 | Cooks et al. ............... 250/288 |
| 4,901,727 | A | * | 2/1990 | Goodwin .................... 600/364 |
| 5,078,755 | A | * | 1/1992 | Tozawa et al. ................. 95/46 |
| 5,317,932 | A | * | 6/1994 | Westlake et al. ......... 73/864.73 |
| 5,448,062 | A | * | 9/1995 | Cooks et al. ............... 250/288 |
| 5,492,838 | A | * | 2/1996 | Pawliszyn ................... 436/178 |
| 5,543,625 | A | | 8/1996 | Johnson et al. ............. 250/427 |

FOREIGN PATENT DOCUMENTS

| | | | |
|---|---|---|---|
| JP | 64-37405 | * | 2/1989 |
| JP | 5-325881 | | 12/1993 |

OTHER PUBLICATIONS

Agren, A. et al, Acta Pharmaceutica Suecica 1967, 4, 1-12.*
Herman, J. J. Recl. Trav. Chim. Pays-Bas 1979, 98, 133-136.*
Eustache, H, et al, Journal of Membrane Science 1981, 8, 105-114.*
Sturaro, A. et al, Analytica Chimica Acta 1989, 224, 119-122.*
LaPack, M. A. et al, Analytical Chemistry 1991, 63, 1631-1637.*
Shelekhin, A. B. et al, Journal of Membrane Science 1992, 73, 73-85.*
Kana, T. M. et al, Analytical Chemistry 1994, 66, 4165-4170.*
Bessarabov, D. G. et al, Ind. Eng. Chem. Res. 1995, 34, 1769-1778.*
LaPack, M. A. et al, Analytical Chemistry 1996, 68, 3072-3075.*
Hartland, S., Transactions of the Institution of Chemical Engineers 1967, 45, T82-T89.*
Pan, C. Y. et al, Industrial & Engineering Chemistry Fundamentals 1974, 13, 323-331.*
Kotiaho et al., "Membrane Introduction Mass Spectrometry," *Analytical Chemistry*, vol. 63, No. 18, Sep. 15, 1991, pp. 875A-883A.
Mastenbrook, Jr. et al., "Ventilation-perfusion ratio distributions by mass spectrometry with membrane catheters," *American Physiological Society*, vol. 53, pp. 770-778, 1982.
Baumgardner et al., "Countercurrent Extraction of Sparingly Soluble Gases for Membrane Introduction Mass Spectrometry," *Annals of Biomedical Engineering*, vol. 25, pp. 858-869, 1997.
Bier et al, "Membrane Interface for Selective Introduction of Volatile Compounds Directly into the Ionization Chamber of a Mass Spectrometer," *Anal. Chem.*, vol. 59, No. 4, Feb. 1987, pp. 597-601.
Boerner eet al., "Direct Mass Spectrometer Analysis of Body Fluids from Acutely Poisoned Patients," *Clinic Chimica Acta*. vol. 49, pp. 445-454, 1973.
I. Jelinek, "Matrix Effects in Membrane Introduction Mass Spectrometry. I. Effect of Poly Ethylene Glycol on Permeation Rate of 1-Octanol Through Silicon Rubber Membrane," *Chemical Papers*, vol. 50, No. 3, pp. 131-137, 1996.
Lewis et al., "Membrane Mass Spectrometer Inlet for Quantitation of Nitric Oxide," *Biological Mass Spectrometry*, vol. 22, pp. 45-52, 1993.
Meyer et al., "Separator Membranes for Mass Spectrometry of Blood Gases: Gas Permeability With Regard to the Measurement of Inert Gases in the Determination of Organ Blood Flows," *Biomedi/inische Technik*, 1988, vol. 33, No. 4, pp. 66-72.
Sahlestrom et al., "Flow-Injection Extraction With A Microvolume Module Based on Integrated Conduits," *Analytica Chimica Acta*, 1986, vol. 185, pp. 259-269.
W. Schaffartzik, "Methods for Determination of Pulmonary Gas Exchange," *Anaesthesist*, 1993, vol. 42, pp. 3-10.
Virkki et al., "On-Site Environmental Analysis by Membrane Inlet Mass Spectrometry," *Anal. Chem.*, Apr. 1995. vol. 67, No. 8, pp. 1421-1425.
Zeineh et al., "Thin-Layer Microtubular Continuous-Flow Countercurrent Dialysis," *Journal of Clinical and Laboratory Medicine*, Apr. 1972, vol. 79, No. 1, pp. 648-656.
S. D. Kolev et al., *Anal. Chim. Acta*, 1993, vol. 268, pp. 7-27.
D. Y. Takigawa, *Sep. Sci. Technol.*, 1992, vol. 27, pp. 325-339.
R. H. Atallah et al., *Anal. Chem.*, 1987, vol. 59, pp. 2909-2914.
D. J. Wilson, *Separation Science and Technology*, 1988, vol. 23, pp. 133-151.

* cited by examiner

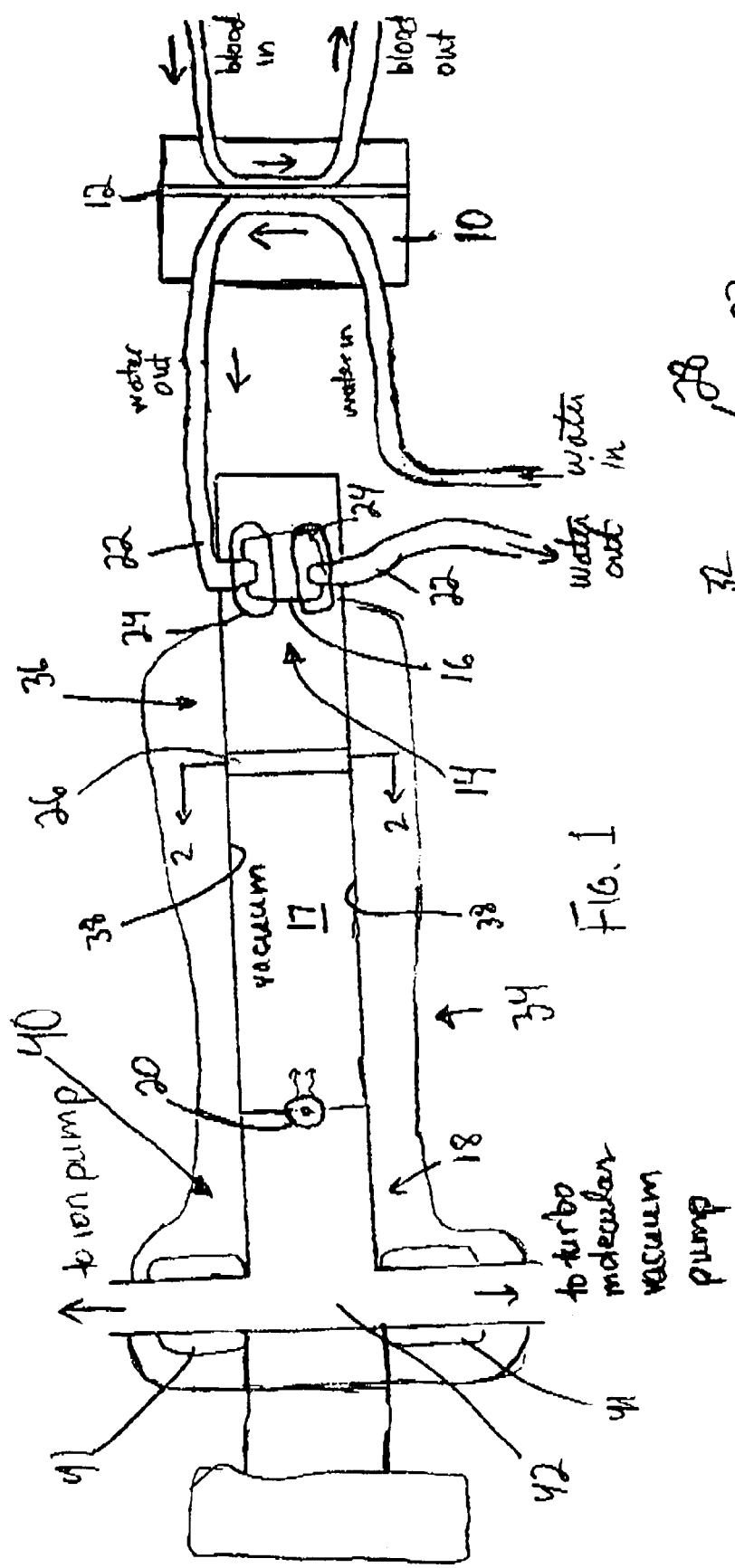
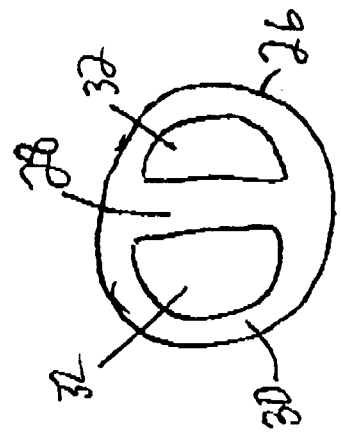
FIG. 1
FIG. 2

US 7,087,436 B2

MEMBRANE COUNTERCURRENT EXCHANGER AND MEMBRANE INLET MASS SPECTROMETER FOR THE ANALYSIS OF GAS PARTIAL PRESSURE IN LIQUID SAMPLES

This is a continuation of U.S. patent application Ser. No. 08/928,099, filed Sep. 12, 1997, now abandoned, which claims the benefit of 60/026,035, filed Sep. 13, 1996.

BACKGROUND OF THE INVENTION

1. Field of the Invention

The present invention relates to a method and apparatus for the analysis of blood or other liquids by mass spectrometry to determine the partial pressures of gases and other volatile substances dissolved in the blood or other liquid, and more particularly, to a countercurrent membrane exchanger for equilibrating a carrier fluid with the sample of blood or other liquid, coupled to a tubular direct insertion membrane probe type of membrane inlet mass spectrometer.

2. Description of the Prior Art

Countercurrent exchange has been widely applied in the fields of heat transfer (for example countercurrent heat exchangers) and mass transfer (for example countercurrent dialysers). Prior applications have used countercurrent exchange to obtain maximal heat or mass transfer in the most efficient way possible, where the objective has been to achieve the smallest exchange area, smallest exchanger size, or minimal energy requirements to drive the liquid flow, for a given exchange rate. No prior use of countercurrent exchange, however, for the purpose of equilibrating a carrier stream gas partial pressure with a sample stream gas partial pressure, specifically to allow measurement of gas partial pressure in the sample with no dependence on gas solubility in the sample, is known to the inventors. The design of a countercurrent exchanger for this analytic purpose (measuring gas partial pressures in liquid samples) is quite different from the design of countercurrent exchangers for maximal transfer rates. More specifically, the inventors are not aware of any prior use of a membrane countercurrent exchanger for the purpose of measuring the partial pressures of gases and other volatile substances in blood, or other fluids, with no dependence on the solubility of the gas or volatile substance in the blood or other fluid.

In the current invention, the partial pressures of gases and volatile substances in the carrier fluid (which has exited the countercurrent membrane exchanger) are measured by use of a tubular direct insertion membrane probe (t-DIMP) as an inlet to a mass spectrometer. Considerable work has been done by others in the area of t-DIMP. For example, Kotiaho et al. describe in an article entitled "Membrane Introduction Mass Spectrometry," *Anal. Chem.*, Vol 63, No. 18, pp. 875A–883A (Sep. 15, 1991) the application of t-DIMP in volatile organic chemical (VOC) analysis and fermentation monitoring. However, no reference can be found relating to the use of Teflon™ sleeves specifically to reduce noise, to the use of radiation shields to allow lower carrier flow rates, and to the heating of the section between the ion source and the vacuum pumps specifically to improve linearity.

Measurement of gas partial pressures in liquid samples has applications in fermentation monitoring, VOC analysis, and in the multiple inert gas elimination technique (MIGET). In the MIGET, gas partial pressures in blood samples are used to define the distribution of ventilation/perfusion ratios in the lung, allowing precise definition of the mechanisms of impaired pulmonary gas exchange. The closest technology similar to the current invention known to the inventors is an attempt to perform rapid MIGET by mass spectrometry (MIGET-MS) by Mastenbrook, Massaro, and Dempsey in the late 1970's and early 1980's. Mastenbrook et. al. published a description of membrane inlet mass spectrometry (MIMS) probes for use in MIGET in blood samples in an article entitled "Ventilation-Perfusion Ratio Distributions By Mass Spectrometry With Membrane Catheters," *J. Appl. Physiol.*, Vol. 53, pp. 770–778 (1982). The membranes they used, commercially available at the time, sampled enough gas from the blood phase to introduce what is known as stirring artifact, referring to the difference in signal between a gas phase and a liquid phase owing to the diffusional resistance in unstirred liquid layers. They suggested calibrating to account for stirring artifact, but because stirring artifact is a function of the gas solubility in blood, this would require a separate calibration for each individual subject. In other words, their design did not overcome the need to equilibrate at least one blood sample per subject with a gas phase to determine solubility, which is the main source of error and analysis time in the traditional MIGET by gas chromatography (MIGET-GC). In addition, they did not specify the time response of their system, but because of the strong adsorption of acetone and diethyl ether to room temperature stainless steel, it is believed that the response speed for these gases would likely be very slow. No further development of this technology has been found by the present inventors.

It is desired to develop a technique for measuring gas partial pressures in liquids, such as blood, which is independent of the solubility of the gas in the sample and thus much more accurate than existing gas partial pressure measurement techniques. The present invention has been designed to meet this need in the art.

SUMMARY OF THE INVENTION

The present invention relates to a method for extracting gases and other volatile substances from a sample of blood or other liquid, and dissolving this gas or volatile substance into a carrier fluid, by use of countercurrent exchange. The gas partial pressure in the carrier fluid is equilibrated to the initial gas partial pressure in the blood or fluid sample. The majority of the gas in the sample can thereby be extracted from the sample, but the measured gas partial pressure in the carrier depends only on the gas partial pressure in the sample and not on the solubility of the gas in the sample. The use of countercurrent exchange therefore allows measurement of gas partial pressures in the liquid sample with no dependence on solubility.

The principles of countercurrent extraction for analysis of gas and volatile substance partial pressures in liquids can be applied using any fluid for the carrier stream, so long as the liquid sample is separated from the carrier stream or immiscible with the carrier stream, and so long as the gases and volatiles can exchange between the sample and carrier streams. The carrier stream, for example could be a gas phase, or an oil that is immiscible with the sample liquid. The design equations developed by the inventors can be applied to determine the flow rates required for any carrier stream. In a preferred embodiment of the present invention, the carrier stream is distilled water, and the carrier stream is separated from the sample of blood, or other liquid, by a gas permeable membrane that allows the gases and volatiles in the sample to diffuse into the carrier. In the preferred embodiment, the gas permeable membrane is a thin silicone membrane, but other types of gas permeable membranes could be used to separate the carrier and sample streams.

After the gas or volatiles in the sample are extracted into the carrier stream in the countercurrent exchanger, the gas or volatile partial pressures in the carrier stream can be analyzed by any suitable technique for measuring gas partial pressures in liquid samples, including mass spectrometry, gas chromatography, and electrochemical techniques. In the preferred embodiment, the gas partial pressures are analyzed with a t-DIMP type of membrane inlet mass spectrometer, with modifications that allow use of the t-DIMP over a wide range of solubilities of gases in water.

Measurement of gas or volatile partial pressures in fluid samples with no dependence on solubility has applications in areas where the object of interest is partial pressure, but the solubility of the gas or volatile in the sample fluid is variable. Examples of applications include: (1) VOC analysis in heavily polluted water samples, where the contaminants such as mud or organic waste lead to variations of the solubility of the VOC in the water samples; (2) analysis of gas partial pressures in the media from biochemical fermentation reactors, where the gas solubility in the media is dependent on pH of the media and the protein and lipid content of the media; and (3) MIGET, in which the retention data are defined solely in terms of inert gas partial pressure in the blood samples, but the inert gas solubility in the blood varies from patient to patient.

BRIEF DESCRIPTION OF THE DRAWINGS

The foregoing and other novel features and advantages of the invention will become more apparent and more readily appreciated by those skilled in the art after consideration of the following description in conjunction with the associated drawings, of which:

FIG. 1 illustrates a countercurrent membrane exchanger connected to a tubular direct insertion membrane probe for gas partial pressure measurement in accordance with a preferred embodiment of the invention.

FIG. 2 illustrates the ion source shield along line 2—2 of FIG. 1.

DETAILED DESCRIPTION OF THE PRESENTLY PREFERRED EMBODIMENTS

Figure 3:
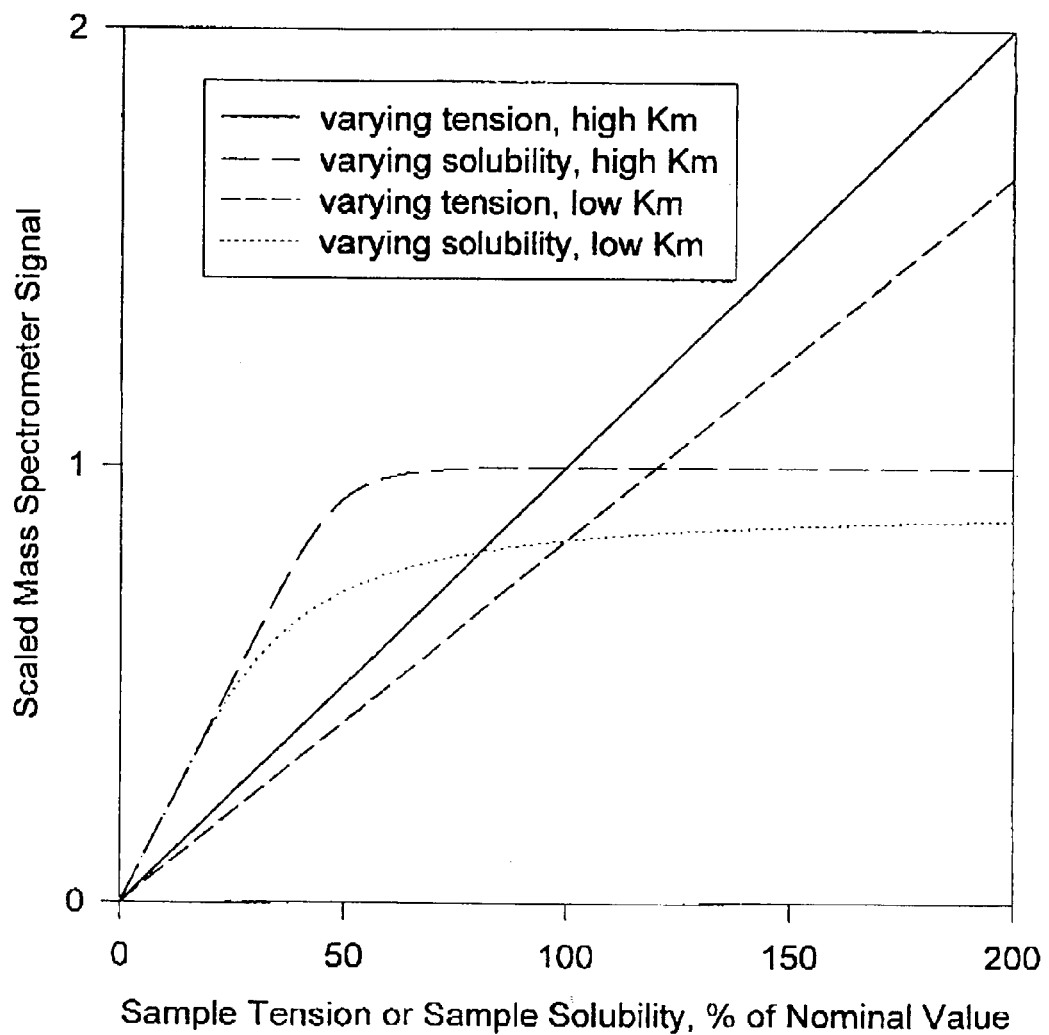
FIG. 3 illustrates the theoretical linear variation of a mass spectrometer signal with sample gas tension, and minimal variation of the signal as gas solubility is varied around the nominal value, for an adequate membrane transfer coefficient ("high Km"), as well as the expected degradations in performance of the countercurrent membrane exchanger of the invention when there is a barrier to diffusion between the sample and carrier streams ("low Km").

A system and technique for achieving the above objects of the invention will be described herein with respect to FIGS. 1–6. Those skilled in the art will appreciate that the description with respect to these figures is for explanatory purposes only and is not intended to limit the scope and application of the invention. The scope of the invention may instead be determined from the attached claims.

As shown in FIG. 1, blood samples or samples of other liquid containing dissolved gases and volatiles are injected at a constant flow rate into the countercurrent membrane exchanger (CCME) 10 of the invention, where the gases and volatiles are extracted from the blood sample into a carrier fluid through a silicone membrane 12. The carrier fluid (e.g., distilled water), also flowing at a constant flow rate, carries the gases and volatiles into a membrane inlet system of a tubular direct insertion membrane probe (t-DIMP) 14 where the gases and volatiles diffuse through a silicone tubular membrane 16 and into the vacuum system 17 housing the mass spectrometer 18. The gases and volatiles diffuse to the ion source 20 of the mass spectrometer 18 where they are ionized and then separated on the basis of mass to charge ratio and analyzed by mass spectrometer 18 using standard techniques. The current measured at an appropriate atomic mass unit (amu) peak by mass spectrometer 18 is directly proportional to the partial pressure of one of the gases in the carrier.

The mass spectrometry technique used in accordance with a preferred embodiment of the invention is preferably capable of carrying out analysis of gas and volatile partial pressures in liquid samples with 1–2 ml, preferably about 1.6 ml, of sample volume, with an analysis time of approximately 10 minutes. The CCME and t-DIMP technique of the invention also may be nearly completely automated, under computer control.

A) The Tubular Direct Insertion Membrane Probe (t-DIMP)

As shown in FIG. 1, the t-DIMP 14, which introduces the gases and volatiles from the water carrier stream into the vacuum system 17 that houses the mass spectrometer 18, consists of a silicone tubing membrane 16 that separates the carrier water from the vacuum system 17 and allows the gases and volatiles to diffuse through the silicone tubing membrane 16 into the vacuum system 17. The silicone tubing membrane 16 is located within the vacuum system 17 and is attached to and supported by stainless steel transit tubing 22 and sealed to the steel transit tubing 22 by Teflon™ heat shrink tubing 24. A complete description including dimensions, materials, and configuration, can be found in a manuscript by the present inventors entitled "Countercurrent Extraction of Sparingly Soluble Gases for Membrane Introduction Mass Spectrometry," *Ann. Biomed. Eng.*, Vol. 25, pp. 858–869 (1997), the contents of which are hereby incorporated by reference.

Several features of the t-DIMP of the invention are unique compared to prior art t-DIMP probes and compared to other prior membrane inlet mass spectrometry (MIMS) systems, and these features are crucial to the accurate measurement of gases and volatiles over a wide range of solubilities, such as the range of solubilities encountered in the MIGET.

First, as shown in FIG. 1, the silicone tubing membrane 16 is attached to the stainless-steel transit tubing 22 by Teflon™ heat shrink tubing 24, laid over the silicone tubing membrane 16 and shrunk to a tight fit with heat application.

Before the addition of the heat shrink tubing 24, the signals for low solubility gases (such as SF6 and krypton) showed substantial noise in the form of characteristic spikes, most likely due to migration of the low solubility gases into small gas bubbles trapped between the silicone tubing membrane 16 and the stainless steel transit tubing 22 and intermittently released into the vacuum system 17. This problem was most pronounced for the low solubility gases, likely because of their substantial partitioning from a water phase to a gas phase, and was completely eliminated by addition of the Teflon™ sleeves 24.

Second, as best depicted in FIG. 2, a simple and unique radiation shield 26 was constructed to prevent radiation from the ion source 20 from heating the silicone tubing membrane 16 directly. The radiation shield 26 consists of a strip of copper 28, oriented parallel to the silicone tubing membrane 16 and located between the silicone tubing membrane 16 and the ion source 20. This copper strip 28 is an integral part of a copper disc 30, with cutouts 32, which also serves as the gasket for the standard knife-edge vacuum joint between the mass spectrometer housing 34 and the t-DIMP support 36. The copper strip 28 shields the silicone tubing membrane 16 from thermal heating from the ion source filaments, and conducts radiated heat to the walls 38 of the vacuum system 17. Without the radiation shield 28, the ion source filaments vigorously heat the silicone tubing membrane 16 and the carrier water inside, making precise temperature control of the silicone tubing membrane 16 difficult and restricting the carrier to high flow rates in order to keep the temperature of the silicone tubing membrane 16 in a suitable range. It should be noted that for samples collected at room temperature (25 C) or at body temperature (37 C), significant heating of the carrier leads to gas supersaturation, bubble formation, and associated noise in the signal that is intolerable. Addition of the radiation shield 28 allows much lower carrier flow rates without supersaturation which, in turn, allows more complete extraction of the gases and volatiles and improved sensitivity. Reducing direct heating of the silicone tubing membrane 16 from the filaments of the ion source 20 also allows more precise control of the temperature of the silicone tubing membrane 16.

Third, as shown in FIG. 1, insulation 40 and heating tapes 41 are arranged around the stainless steel vacuum system 17 to assure that there is a steady increase in the temperature of the wall 38 between the ion source 20 and the entrance 42 to the pumping section. This arrangement was found to be essential to achieve a linear relationship between signal and gas partial pressure for several high solubility gases (acetone, diethyl ether, enflurane, and desflurane). For similar membrane inlet mass spectrometer (MIMS) systems, linearity between gas partial pressure at the ion source and current signal is almost universally assumed. It was found, however, that the metal vacuum housing between the ion source and the pumping sections, if allowed to cool below the wall temperature at the ion source, behaves as a saturable binding site for some soluble gases, attenuating the signal in a concentration-dependent fashion, leading to marked nonlinearity. Controlled heating of this crucial intervening section in accordance with the invention restored linearity and in addition provided a significant increase in sensitivity for these soluble gases.

The t-DIMP 14 of FIG. 1 is designed specifically for the analysis of gas partial pressures in carrier fluid coming from a CCME 10, and more specifically, for the analysis of the six inert gases suitable for MIGET As described herein, the t-DIMP 14 of FIG. 1 is accurate enough to use for analysis of all six MIGET gases in a specified solution with constant and known gas solubilities, such as albumin. This t-DIMP 14 can therefore be applied directly to the MIGET in certain experimental models of lung disease and injury that use such artificial perfusates instead of blood. This t-DIMP 14, however, has other potential applications. First, directly related to MIGET as performed in patients, variations in solubility are not a problem if the perfusate is a known solution with known properties, for example saline solution or albumin solution. Therefore, for certain experimental preparations that use a non-blood perfusate, the t-DIMP system can be applied directly to the measurement of 6 inert gases and to MIGET, without the CCME 10. In other words, when solubility is known not to vary, the countercurrent membrane exchanger 10 is not needed and the t-DIMP 14 can be used directly for MIGET. One application of the t-DIMP system of FIG. 1, therefore, is direct use for MIGET in experimental preparations that use a known perfusate.

The unique feature of heating the t-DIMP 14 to provide linearity, described above, would also find useful application in other areas where t-DIMP is commonly used, in particular the analysis of trace volatile organic contaminants (VOC) in aqueous solutions, and in process monitoring for biochemical fermentation reactions. Traditionally, t-DIMP systems are assumed to be linear but research by the inventors shows that this is not always the case, and the novel application of heat to the vacuum system walls 38 between the ion source 20 and the pumping section can restore linearity for some systems.

The radiation shield 28 also has useful applications in other areas where t-DIMP is commonly used, i.e., VOC analysis and fermentation monitoring. The lower sample flow rates that are made possible by reduced heating of the t-DIMP membrane could be advantageous in many situations where improved sensitivity would be desirable.

The reduction of signal noise with the Teflon™ sleeves described above would also be advantageous for other t-DIMP applications, particularly those applications involving low solubility gases.

In a tubular DIMP, water (or blood) samples are pumped through polymer tubing that is located within the mass spectrometer vacuum system, in close proximity to the ion source. Gases, volatiles, and water diffuse through the polymer membrane and desorb directly into the vacuum system, with the membrane serving to prevent convective transport of the water into the vacuum system and gross contamination. The partial pressure (or tension) of the insert gas ($P_{crd}$) decreases exponentially as the sample traverses the DIMP tubing:

$$P_{crd} = P_{cr0} e^{-\beta y}, \quad \text{(D-1)}$$

where $P_{cr0}$ is the entering inert gas tension, y is the axial distance along the DIMP tubing, and $\beta$ is defined by:

$$\beta = \frac{2\pi \alpha_{dmp} D_{dmp}}{\ln(b/a) V_{cr} \alpha_{cr}} \quad \text{(D-2)}$$

where a and b are the inner and outer diameters of the tubing, $\alpha_{dmp}$ and $D_{dmp}$ are the solubility and diffusivity of the gas in the membrane polymer, $\alpha_{cr}$ is the gas solubility of the gas in the liquid passing through the DIMP, and $V_{cr}$ is the flow rate of the liquid passing through the DIMP. Equation D-1 is readily derived by a mass balance on a differential element of the DIMP tubing and integration of the resulting first-order ordinary differential equation, assuming a flat velocity profile, negligible axial dispersion compared with axial convection, and negligible radial resistance to diffusion in the water phase, compared with the radial resistance of the membrane.

For most applications using inert tracer gases in physiology, the variable of interest is gas partial pressure (or tension) in a blood sample rather than inert gas concentration. For example, in the MIGET, gas retention and excretion are defined in terms of ratios of the arterial, mixed venous, and mixed expired gas tensions. It is therefore desirable to obtain a mass spectrometer signal that is linearly related to the gas tension in the blood. In addition, it is known that the solubility of inert gases in blood varies from patient to patient, with a coefficient of variation (standard deviation/mean) of up to 15.5%. It is therefore also desirable that the mass spectrometer signal be independent of the solubility in the blood. For a small β-value in Eq. D-1 (e.g., for tubing with low permeability), the gas tension throughout the DIMP will be approximately equal to the entering gas tension, in which case the gas sample rate into the mass spectrometer $Q_{ms}$ can be given by:

$$Q_{ms} = \frac{2\pi\alpha_{dmp}D_{dmp}L_{dmp}P_{cr0}}{\ln(b/a)} \quad (D-3)$$

where $L_{dmp}$ is the length of the DIMP tubing. With selective peak monitoring at an appropriate mass/charge ratio, and appropriate vacuum system design, the mass spectrometer signal is directly proportional to the gas sample rate $Q_{ms}$. Although this approach, in which the blood sample would be injected directly into the DIMP, produces the desired linear dependence of signal on gas tension and independence from solubility, sensitivity is compromised by wasting of the majority of the gas sample.

Counter Current Extraction

An alternative approach is to equilibrate the blood sample with a water carrier stream in a countercurrent exchanger (CCE), in which the exiting carrier gas tension is nearly equal to the entering sample tension, but the exiting sample gas tension approaches the entering carrier tension of 0, thereby allowing nearly complete extraction of the gas without introducing solubility dependence. The gas sample in the carrier is then transported to the DIMP. When extraction of gas in the DIMP is significant. EQ. D-3 no longer applies and the gas sample rate is given by Eq. D-4:

$$Q_{ms}=[\alpha_{cr}V_{cr}(1-e^{-\beta L_{dmp}})]P_{cr0} \quad (D-4)$$

In this approach, the DIMIP is designed with a very permeable membrane, and the tubing length and carrier flow are adjusted to approach complete extraction. This design of the DIMP not only makes maximal use of the entire gas sample in the carrier, it has the additional advantage that, for large values of β, the gas sample rate is independent of membrane properties $\alpha_{dmp}$ and $D_{dmp}$ and independent of variations of water solubility with temperature, thus eliminating dependence of the mass spectrometer signal on the temperature of the membrane. For gases that are not extracted in one pass through the DIMP, the mass spectrometer signal will still be linearly dependent on the carrier gas tension, provided that the membrane temperature is held constant.

B) The Countercurrent Membrane Exchanger (CCME)

Unlike the artificial perfusates used in experimental models, measurement of gas partial pressures in many liquid samples, including blood samples, adds the additional complexity that the solubility of these gases in the samples varies between samples. Measurement of gas and volatile partial pressures in many liquid samples therefore requires either: (1) a technique that measures the gas partial pressures without any dependence on solubility; or (2) measurement of the gas solubility along with the gas partial pressure and then correction of the measured partial pressure to account for the individual solubility. The latter approach, however, adds significantly to the required analysis time and adds sources of measurement error. For example, measurement of gas solubility represents a substantial part of both the sources of error and the analysis time for the conventional MIGET.

Partial pressures of gases in liquids could also be measured by membrane inlet mass spectrometry. (MIMS) with no solubility dependence, by use of a high resistance membrane that extracts minimal gas from the liquid. This approach, however, reduces the sensitivity of the measurement because the unextracted gas in the sample is essentially wasted.

The CCME 10 illustrated in FIG. 1 solves this dilemma by extracting gases and volatiles from the liquid sample into a water carrier phase with the flow streams arranged countercurrent. Because the gas partial pressure in the exiting carrier is equilibrated with the gas partial pressure in the entering sample, dependence of the measured gas partial pressure on gas solubility in the sample is eliminated. However, nearly all of the gas can be extracted from the liquid sample, boosting the sensitivity 50 fold or more.

A complete description of the CCME principles and complete details on a working model are provided in the aforementioned manuscript entitled "Countercurrent Extraction of Sparingly Soluble Gases for Membrane Introduction Mass Spectrometry". Briefly, the CCME 10 consists of two flow channels, one for the carrier (e.g., water) and one for the liquid sample, separated by a silicone membrane 12, with channel dimensions and flows optimized to provide adequate equilibration in the exchanger 10 and an optimal signal for the gas partial pressures.

The inventors have developed the design equations describing the performance of a CCME 10 that equilibrates a sample fluid (e.g., blood) and a water carrier, when the sample streams and carrier streams are held at different flow rates and the dissolved gases and volatiles have different solubilities in the sample and carrier streams. These design equations were used to optimize the behavior of the CCME 10. With appropriate design, the mass spectrometer signal was found to be linearly dependent on gas partial pressure in the sample but independent of variations in the gas solubility in the sample over a wide range of gas solubilites, as shown in FIG. 3. FIG. 3 illustrates the theoretical linear variation of a mass spectrometer signal with sample gas tension, and minimal variation of the signal as gas solubility is varied around the nominal value, for an adequate membrane transfer coefficient ("high Km," where Km is a membrane transfer coefficient for gas diffusion across the countercurrent exchanger membrane 12), as well as the expected degradations in performance of the countercurrent membrane exchanger 10 of the invention when there is a barrier to diffusion between the sample and carrier streams ("low Km").

In particular, the linear dependence of mass spectrometer signal on gas partial pressure in the sample, $P_{s0}$, is illustrated by the linear dependence of the gas partial pressure in the carrier exiting the CCME, $P_{crex}$, on $P_{s0}$:

$$P_{crex} = (\zeta) P_{s0} \quad (1)$$

where zeta is defined by $$\zeta = \frac{e^{K_m \gamma L_{cce}} - 1}{e^{K_m \gamma L_{cce}} - \frac{V_{cr} \alpha_{cr}}{V_s \alpha_s}} \quad (2)$$

and gamma is defined by:

$$\gamma = \frac{1}{V_{cr} \alpha_{cr}} - \frac{1}{V_s \alpha_s} \quad (3)$$

and where $K_m$ is a membrane transfer coefficient for gas diffusion across the countercurrent exchanger membrane 12, $L_{cce}$ is the length of the CCME membrane 12, $V_{cr}$ is the carrier volumetric flow rate, $V_s$ is the sample volumetric flow rate, $\alpha_{cr}$ is the solubility of the gas in the carrier, and $\alpha_s$ is the solubility of the gas in the sample.

$K_m$, the membrane transfer coefficient, is defined by its gas solubility $\alpha_{cce}$, its gas diffusivity $D_{cce}$, the membrane width $W_m$ and membrane thickness $\delta_m$ as follows:

$$K_m = D_{cce} \alpha_{cce} \frac{W_m}{\delta_m} \quad (4)$$

The gas partial pressure of the sample at a point x along the countercurrent exchanger:

$$P_s = P_{s0} - \phi(e^{k_m \phi x} - 1) \quad (5)$$

where the parameter $\phi$ is defined as:

$$\phi = \frac{P_{s0} - P_{cren}}{\frac{V_s \alpha_s}{V_{cr} \alpha_{cr}} e^{K_m \gamma L_{cce}} - 1} \quad (6)$$

and $P_{cren}$ is the gas partial pressure of the carrier stream where it enters the countercurrent exchanger. Assuming an entering carrier tension of 0, from Eq. (1) we get the proximal equilibration simply as:

$$\frac{P_{crex}}{P_{s0}} = \zeta \quad (7)$$

At $x = L_{cce}$, from Eqs. (2), (5) and (6), we then get:

$$P_{sL} = P_{s0} \left[ 1 - \frac{V_{cr} \alpha_{cr}}{V_s \alpha_s} \zeta \right] \quad (8)$$

giving the distal extraction as:

$$\frac{P_{s0} - P_{sL}}{P_{s0}} = \frac{V_{cr} \alpha_{cr}}{V_s \alpha_s} \zeta \quad (9)$$

where $P_{sL}$ is the gas partial pressure in the sample stream as it exits the CCE.

Figure 7:
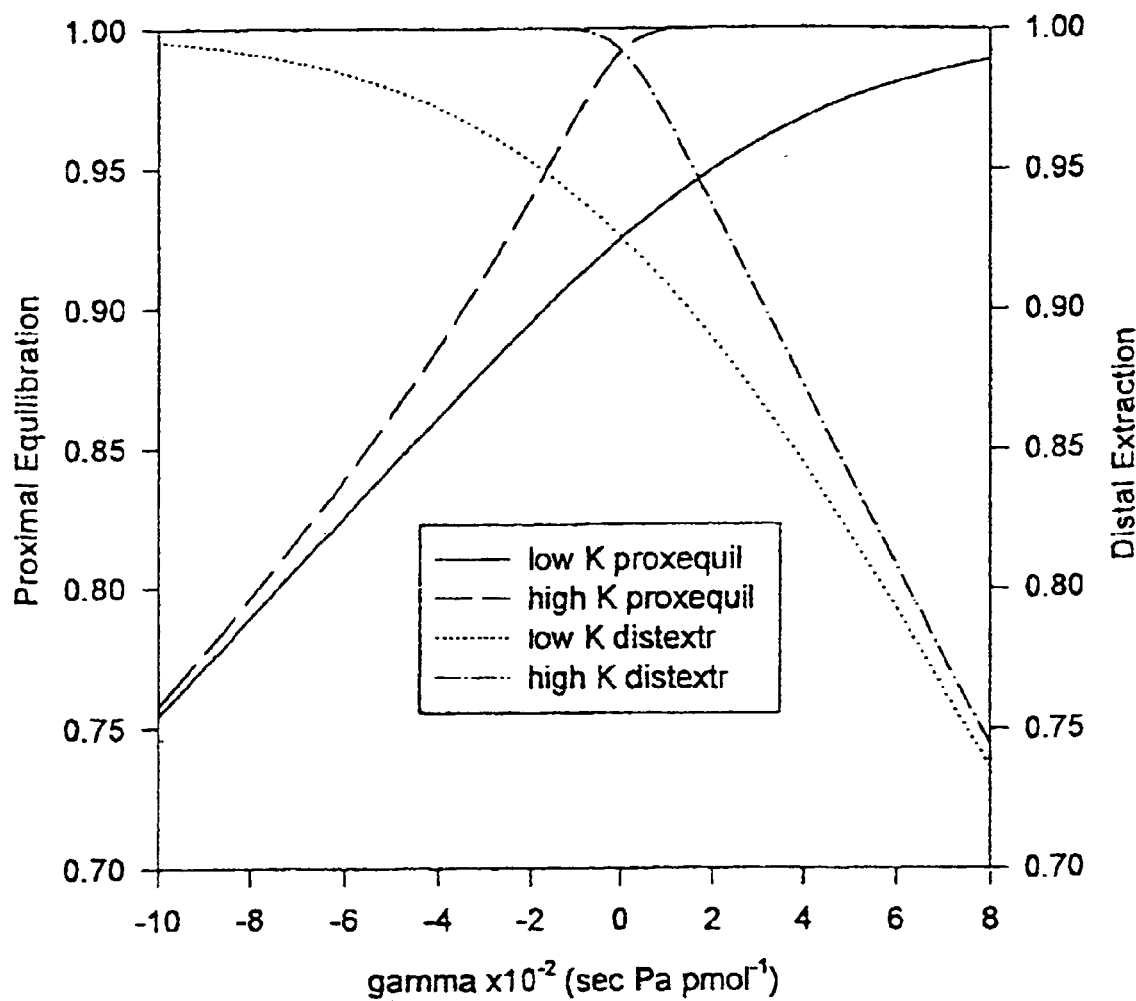
FIG. 7 shows calculated proximal equilibration (proxequil) and distal extraction (distextr) in the CCE as a function of $\gamma$ varied by varying the sample flow rate.

FIG. 7 shows the variation in proximal equilibration (i.e., equilibration at the exiting carrier stream) and distal extraction (i.e., extraction at the exiting liquid stream) with changes in γ. The plot illustrates a range of positive γ for which there is good proximal equilibration despite large variations in γ. In this range, distal extraction is <100%, but is large enough to make use of most of the available gas sample. More particularly, FIG. 7 shows the proximal equilibration (proxequil) and distal extraction (distextr) curves in the countercurrent exchanger as a function of γ varied by varying the sample flow rate $V_s$. The figure also shows the reduced range of proximal equilibration that results from reductions in the membrane transfer coefficient. In this example, the "low K" is roughly 1/215 of the estimated membrane transfer coefficient, while the "high K" is 10 times larger.

The minimal variation of proximal equilibration with variations in γ, for γ>0, suggests that the desired independence of mass spectrometer signal from solubility can be achieved by designing the countercurrent exchanger with a large positive γ. In FIG. 3, the entering sample partial pressure was set to 3,683 ppm, the entering carrier tension for the DIMP was set to the exiting carrier tension from the CCE, and the mass spectrometer signal is normalized to the expected signal at the operating point. Parameters for the DIMP were set to match the experimental apparatus: length of 0.28 cm, silicon tubing of 0.051 cm i.d., and 0.22 cm wall thickness, with the membrane held at 37° C. and the gas solubility and diffusivity in the membrane identical to the values used for the CCE silicone membrane. The plot illustrates a linear relationship between the sample partial pressure and the mass spectrometer signal, with negligible dependence of the signal on the gas solubility in the sample. At the operating point, the distal extraction is 50%. FIG. 3 also shows the expected degradation in CCE performance when the membrane transfer resistance is increased.

The independence of mass spectrometer signal from gas solubility in the samples shown in FIG. 3 is more complicated, but is also given implicitly by Equation 1 above.

Figure 4:
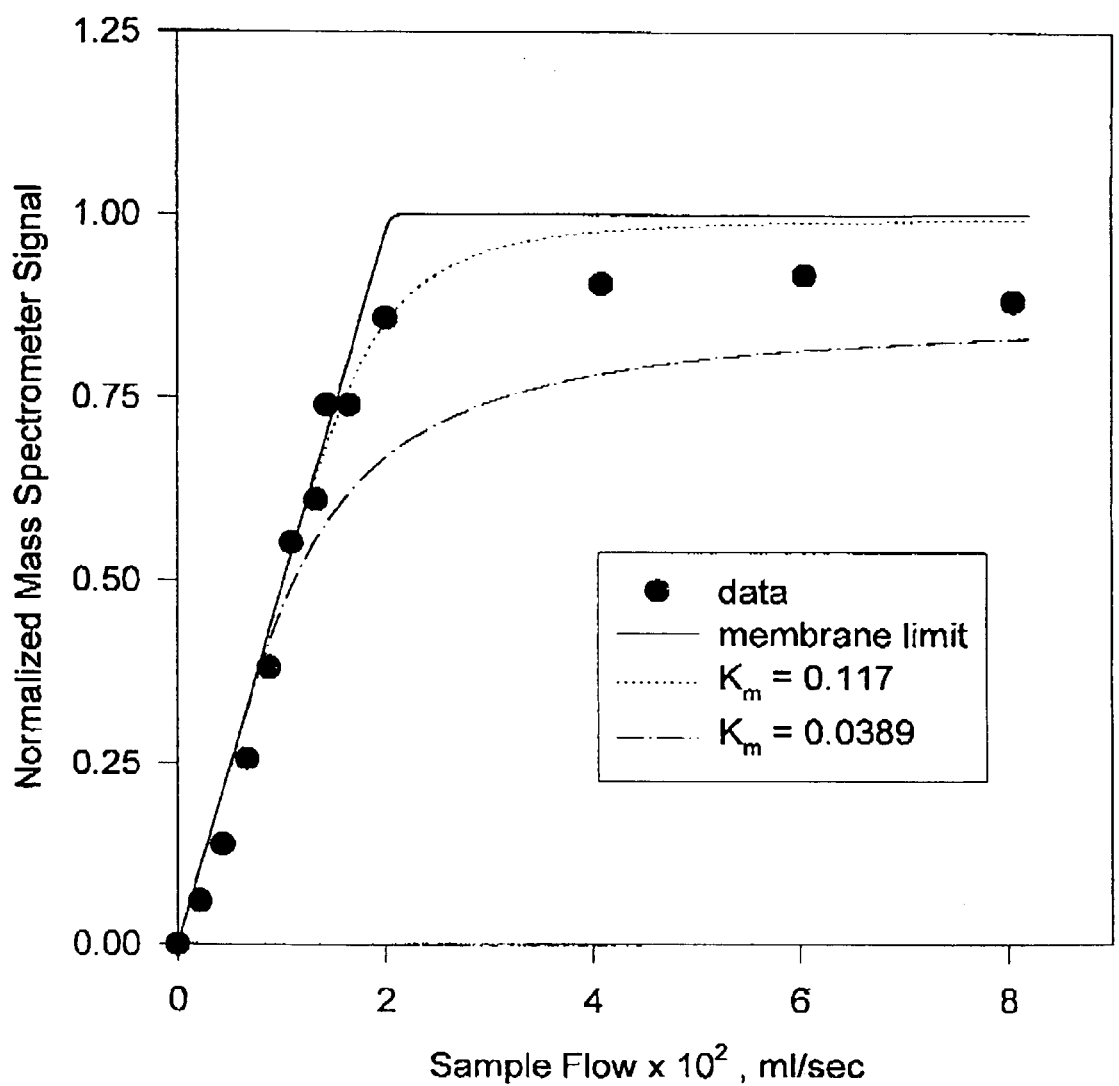
FIG. 4 is a plot of the mass spectrometer signal for krypton as the sample flow is varied, at constant carrier flow, scaled to the signal for the equilibrated carrier, as well as the theoretical plots for membrane limited Km, and two effective Km values that bracket the data.

The major limitation for the CCME 10 is the barrier to equilibration between the sample and carrier streams, due to the high resistance to diffusion of low solubility gases through an aqueous phase. This barrier to equilibration is illustrated in FIG. 4, which is a plot of the mass spectrometer signal for krypton as the sample flow is varied, at constant carrier flow, scaled to the signal for the equilibrated carrier. The illustrated data is from a CCME 10 with linear flow channels. Also shown are the theoretical plots for membrane limited Km, and two effective Km values that bracket the data. Incomplete equilibration due to a diffusion barrier in such a linear CCME is apparent.

The data for FIG. 4 was collected using the configuration of FIG. 1 as follows. Sulfur hexafluoride (SF6) and krypton (Kr) were analyzed with a UTI 100C quadrupole mass spectrometer 18 using single peak monitoring (m/e=127 for SF6 and m/e=84 for krypton). Emission current (tungsten filaments) was set to 1.40 mA in a closed ion source 20, and electron multiplier high voltage was set to 1655 V for a gain of $1.2 \times 10^5$ (at m/e=28). The mass spectrometer 18 was housed in a stainless steel vacuum system 17 pumped by a Baltzer TPU 170 turbomolecular pump, backed by an Alcatel 2004A rotary vane pump.

One 12.5 cm length, 3.81 cm tube OD vacuum nipple (Huntington Laboratories Inc.) was fitted over the closed ion source 20 and attached to the quadrupole vacuum housing 17. A second nipple was attached to a blank 7.0 cm OD vacuum flange, fitted with two pieces of 316 stainless steel tubing 22 (0.051 cm ID, 0.159 cm OD, 25.4 cm length) for the inlet and outlet to the t-DIMP silicone tubular membrane 16. The tubing pieces were tapered at the vacuum end and bent 90 degrees to align the lumens to face each other, then 0.051 cm ID, 0.094 cm OD silicone tubing membrane 16 (Dow Corning) was stretched over the tapered tubing ends to form the t-DIMP 14 (exposed membrane length of 0.28 cm). The two vacuum nipples were joined by a standard knife edge high vacuum fitting, with the standard copper gasket replaced by copper disk 30. Cutouts 32 in the copper disk 30 allowed molecular flow of gases, while a central linear strip of copper 28 shielded the t-DIMP silicone tubular membrane 16 from direct radiation from the filaments of the ion source 20. The temperature of the carrier water exiting from the DIMP tubing was monitored by a sheathed thermocouple probe, 0.0254 cm OD (Omega), inserted retrograde into the exit tubing to place the sensor in close proximity to the t-DIMP silicone tubular membrane 16. The blank vacuum flange with the DIMP inlet and exit tubing was heated or cooled (depending on the carrier water flow rate) as necessary to maintain the temperature of the t-DIMP 14 at 37 C.

A membrane countercurrent exchanger 10 was constructed from two brass bars (14.9 by 0.635 by 1.27 cm), milled to a flat surface and equipped with alignment pins and clamping screws. Rectangular grooves were machined into the bars, both grooves 12.2 cm in length and 0.0787 cm in width, with a depth of 0.0483 cm for the water carrier channel and a depth of 0.0787 cm for the sample channel. 0.159 cm OD stainless steel connection tubing, 0.0762 cm ID for the sample side and 0.051 cm ID for the carrier side, was fitted to the ends of the channels. A 0.0076 cm thick silicone membrane 12 (Membrane Products Corporation), 0.238 cm wide and 12.5 cm long, served as the exchange membrane separating the flow channels, as well as the gasket sealing the edges of the flow channels. The entire CCME 10 was immersed in a water bath held at 37 C.

Distilled water was used both as the carrier and as the sample fluid. Flow rate in the water carrier stream was controlled by a syringe pump (Harvard Apparatus) and a second syringe pump (Braintree Scientific Corporation) controlled the flow rate in the water sample stream. Transit tubing 22 between the syringe pumps, the CCME 10, and the t-DIMP 14 was 0.159 cm OD, 0.102 cm ID 316 stainless steel tubing, with short lengths of 0.08 cm ID, 0.41 cm OD Tygon® tubing (Cole-Parmer) for connections.

Gas equilibrations were carried out by five exchanges of a gas phase with water in a glass syringe, using premixed tanks of 3683 ppm SF6 in nitrogen or 3775 ppm krypton in nitrogen. Following the fifth exchange, the syringe was placed in a water bath at 37 C for 30 minutes, then thoroughly mixed, and the gas phase was expelled.

Figure 5A:
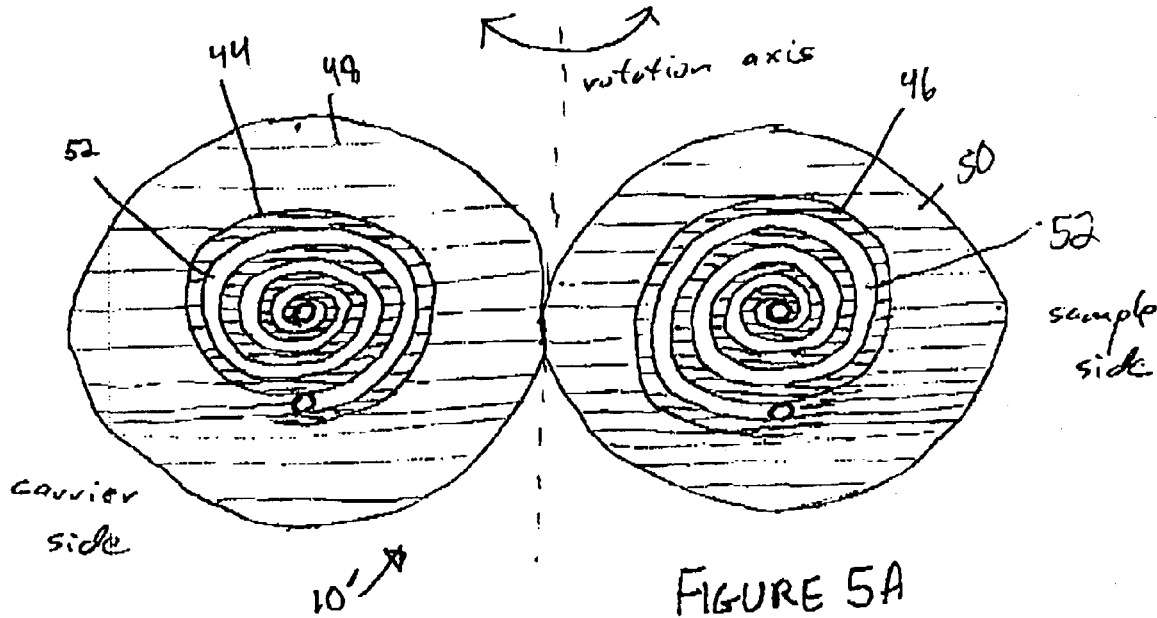
FIGS. 5A–5C illustrate in schematic form a countercurrent membrane exchanger with spiral channels in accordance with a preferred embodiment of the invention.
Figure 5B:
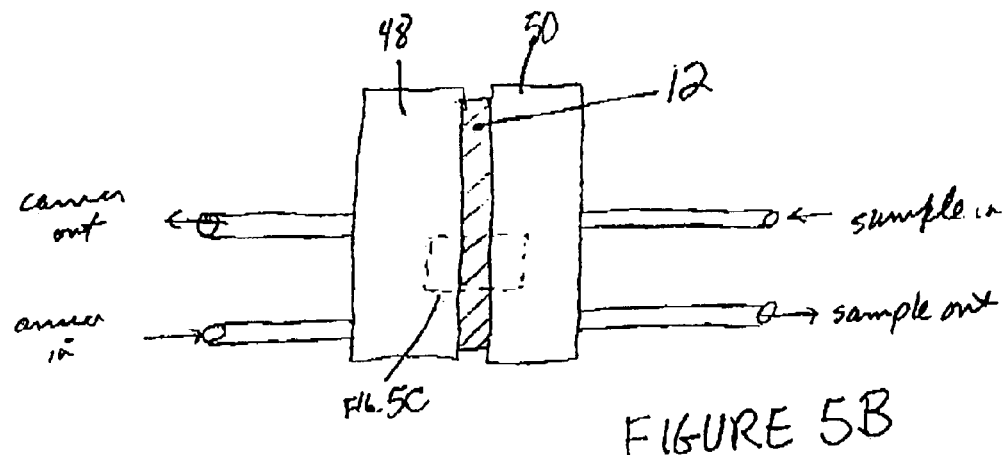
Figure 5C:
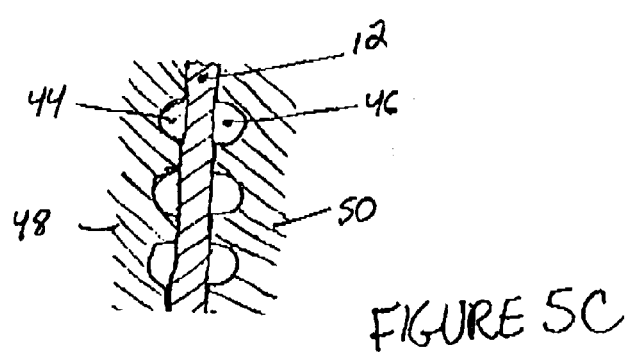

An improved version of the CCME 10 has been constructed that utilizes the secondary flows that arise in a coiled flow channel, as shown in FIG. 5. FIG. 5A is a face view of two opposing steel plates of a CCME 10' rotated so that the spiral grooves in the plates can be seen. FIG. 5B illustrates the CCME 10' of FIG. 5A when the plates are rotated back together and separated by silicone membrane 12, while FIG. 5C illustrates an enlarged cutaway view of the rectangular section outlined in FIG. 5B.

As best illustrated in FIG. 5A, CCME 10' includes, for both the liquid sample flow channel and the water sample flow channel, spiral flow channels 52, semicircular in cross-section, having respective diameters of approximately 0.020 inches. The spiral flow channels 52 are formed by machining spiral grooves 44 and 46 into the flat surfaces of respective stainless steel plates 48 and 50 as shown, cut so that the rings of the channel 52 in the spiral are separated by flat metal grooves 44 and 46 also approximately 0.020 inches wide. These two spiral grooves 44 and 46, in complementary flat plates 48 and 50, are precisely aligned to face each other, and are separated by a flat silicone membrane 12, approximately 0.003 inches thick, as shown in FIGS. 5B and 5C. The secondary flows induced by the spiral grooves 44 and 46 greatly reduce the resistance to equilibration between the liquid sample and water carrier phases, as shown for krypton in FIG. 6.

Figure 6:
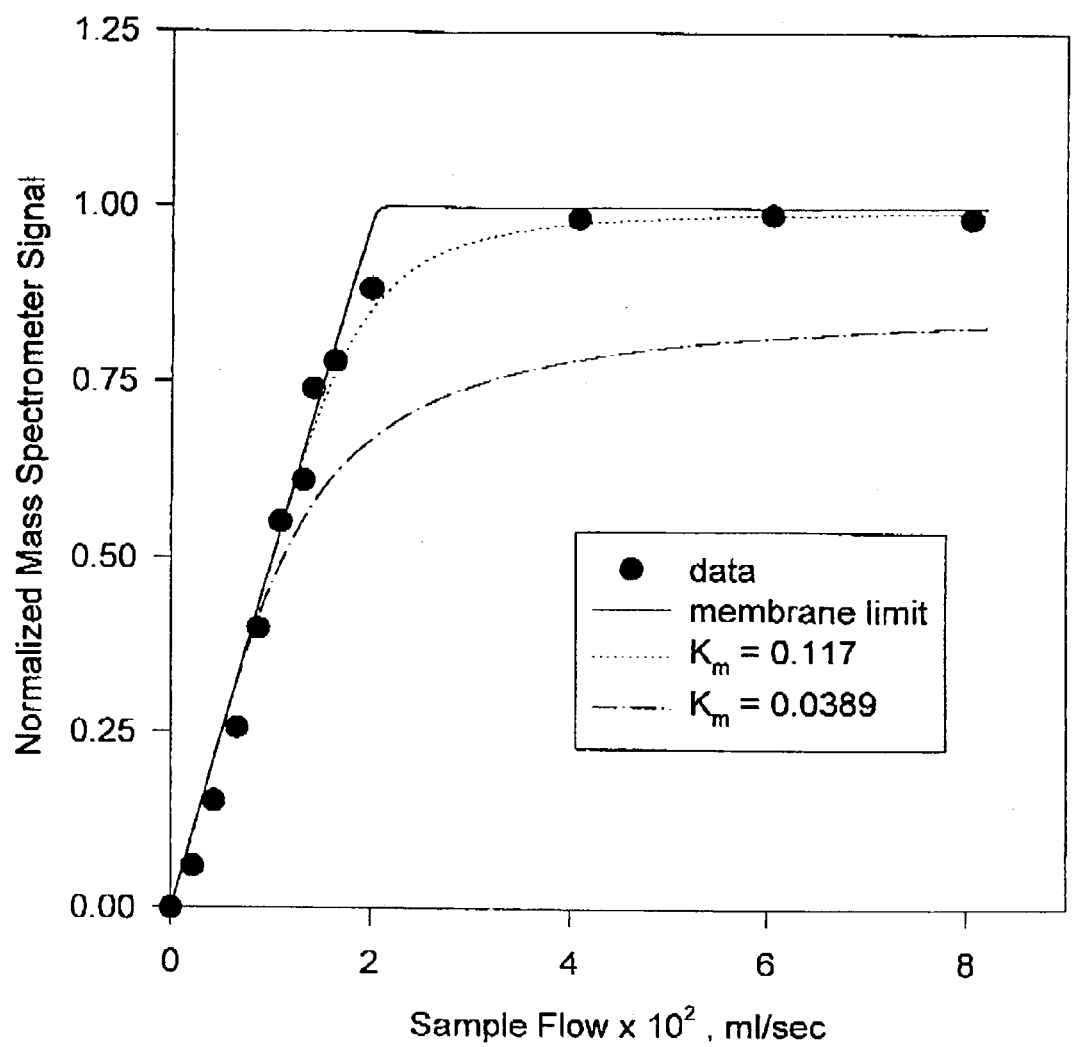
FIG. 6 is a plot of the mass spectrometer signal for krypton as sample flow is varied in a manner similar to FIG. 4, but the data is taken from a countercurrent membrane exchanger that uses the spiral grooves in the embodiment of FIG. 5.

FIG. 6 is a plot of the mass spectrometer signal for krypton as sample flow is varied in a manner similar to FIG. 4, but the data is taken from a countercurrent membrane exchanger 10' using spiral channels 44 and 46 as illustrated in FIGS. 5A–5C. The improved equilibration due to the induced secondary flows is apparent.

The CCME described above was designed specifically for carrying out MIGET by mass spectrometry (MIGET-MS) and is an integral part of the MIGET-MS. This technology, however, would be useful in many other applications. For example, an appropriately designed CCME could provide concentration measurements that are independent of variations in solubility with a boost in sensitivity of up to 90 fold, in any application where variations of solubility in the sample are of concern. In fermentation monitoring, for example, solubility of volatile components in the fermentation broth are a function of the changing protein and cell concentrations. In VOC analysis, some variation in solubility would be expected between water samples of different sources.

The CCME of the invention would also find useful application in other areas of biology besides the MIGET method. Measurement of inert gas partial pressures in blood have been and are being used for measurements of blood flow in several tissues. Use of CCME would allow measurements of gas partial pressures that are independent of variations in gas solubility in blood.

Those skilled in the art will appreciate that these and numerous other applications of the invention, as well as numerous modifications of the invention, may be made within the scope of the invention. For example, if the carrier fluid and the sample are immiscible, as if the carrier is gas bubbles and the sample is blood, the countercurrent exchange of the invention may take place without a membrane. In addition, those skilled in the art will appreciate that other geometries besides the spiral geometry illustrated in FIG. 5A for improving radial mixing may be used to induce secondary flows along the CCME membrane to improve equilibration. Accordingly, all such modifications and applications are intended to be included within the scope of the invention as defined in the following claims.

We claim:

1. A tubular direct insertion membrane probe (t-DIMP) type mass spectrometer system, comprising, in combination:
   a countercurrent exchanger (CCE) for receiving a liquid having a gas dissolved therein and a carrier fluid, the CCE comprising a first membrane across which said gas diffuses from the liquid into the carrier fluid;

a tubular direct insertion membrane probe comprising a silicone tubing membrane configured to receive carrier fluid exiting the CCE;
an ion source configured to direct radiation in a direction of the silicone tubing membrane; and
a radiation shield disposed between said ion source and said silicone tubing membrane so as to block a line of sight from said ion source to said silicone tubing membrane so as to prevent direct heating of the silicone tubing membrane by said ion source.

2. The mass spectrometer system according to claim 1, wherein:
the ion source and the radiation shield are both positioned within a vacuum housing of a mass spectrometer; and
gas in the carrier fluid that diffuses through the silicone tubing membrane travels past the radiation shield and towards the ion source.

3. The mass spectrometer system according to claim 1, wherein said radiation shield is disposed so as to conduct heat radiating from said ion source to walls of said vacuum housing.

4. The mass spectrometer system according to claim 1, further comprising an insulating sleeve disposed between said silicone tubing membrane and a tube connecting to said CCE.

5. The mass spectrometer system according to claim 4, wherein said insulating sleeve is a polytetrafluoroethene heat shrink tube which is shrunk to fit about said silicone tubing membrane and said tube connecting to said CCE.

6. The mass spectrometer system according to claim 1, wherein the CCE is configured to equilibrate said carrier fluid with said liquid such that a gas partial pressure of the liquid entering the CCE is substantially similar to a gas partial pressure of the carrier fluid exiting the CCE.

7. The mass spectrometer system according to claim 1, wherein the CCE comprises first and second plates having respective complementary channels formed therein with the first membrane separating said channels, said respective complementary channels respectively passing said liquid and said carrier fluid in opposing directions adjacent said first membrane so as to permit said gases and volatile substances to pass from said liquid through said first membrane to said carrier fluid.

8. The mass spectrometer system according to claim 7, wherein said channels of said first and second plates are spiral in shape and semicircular in cross-section.

9. The mass spectrometer system according to claim 8, wherein said first membrane is made of silicone.

10. A method for determining the partial pressure of at least one gas dissolved in a liquid in a manner which is substantially independent of the solubility of said gas in said liquid, comprising the steps of:
introducing a carrier fluid and said liquid into a countercurrent exchanger in which said at least one gas passes from said liquid to said carrier fluid;
passing carrier fluid that exits the countercurrent exchanger through a tubular direct insertion membrane probe (t-DIMP) to remove said at least one gas from the carrier fluid; and
providing an ion source configured to direct radiation in a direction of the silicone tubing membrane; and
providing a radiation shield between said ion source and said silicone tubing membrane so as to block a line of sight from said ion source to said silicone tubing membrane so as to prevent direct heating of the silicone tubing membrane by said ion source; and measuring said partial pressure of said at least one gas removed from said carrier fluid using a mass spectrometer.

11. An apparatus for determining the partial pressures of gases and other volatile substances dissolved in a liquid in a manner which is substantially independent of the solubility of said gases and other volatile substances in said liquid, comprising:
a countercurrent exchanger (CCE) which equilibrates a carrier fluid with a sample of said liquid;
a tubular direct insertion membrane probe (t-DIMP) which removes gases and volatile substances from said carrier fluid after it has been equilibrated, said t-DIMP comprising a silicone tubing membrane;
a mass spectrometer which measures said partial pressures of gases and volatile substances removed from said equilibrated carrier fluid by said t-DIMP, wherein said mass spectrometer comprises an ion source configured to direct radiation in a direction of said silicone tubing membrane, and a radiation shield disposed between said ion source and said silicone membrane to block a line of sight from said ion source to said silicone membrane so as to prevent direct heating of the silicone membrane and the carrier fluid, wherein the ion source and the radiation shield are housed within a vacuum housing of the mass spectrometer; and
first and second pumps configured to control flow rates of said sample and said carrier fluid and the liquid containing the sample, such that a gas partial pressure of the carrier fluid exiting the countercurrent exchanger is substantially similar to a gas partial pressure of the sample entering the countercurrent exchanger.

12. An apparatus according to claim 11, wherein said CCE comprises first and second plates having respective complementary channels formed therein and a first membrane for separating said channels, said respective complementary channels respectively passing said liquid and said carrier fluid in opposing directions adjacent said first membrane so as to permit said gases and volatile substances to pass from said liquid through said first membrane to said carrier fluid.

13. An apparatus according to claim 12, wherein said channels of said first and second plates are spiral in shape and semicircular in cross-section.

14. An apparatus according to claim 13, wherein said first membrane is made of silicone.

15. An apparatus according to claim 11, further comprising:
an inlet tube which provides said equilibrated carrier fluid from said CCE to said t-DIMP and an outlet tube which expels water from t-DIMP, said silicone tubing membrane connected to an inlet side of said inlet tube and an outlet side of said outlet tube; and
an insulating sleeve disposed about the connections between said silicone tubing membrane and said inlet and outlet tubes so as to substantially prevent said gases from leaking out at said connections in a non-uniform manner;
wherein said insulating sleeve is a polytetrafluoroethene heat shrink tube which is shrunk to fit about said membrane and said inlet and outlet tubes at said connections.

16. An apparatus according to claim 11, wherein said radiation shield is disposed so as to conduct heat radiating from said ion source filament to walls of said vacuum housing.

17. A method for determining the partial pressures of gases and other volatile substances dissolved in a liquid in a manner which is substantially independent of the solubility of said gases and other volatile substances in said liquid, comprising the steps of:

introducing a carrier fluid and a sample of said liquid into a countercurrent exchanger in which said gases and other volatile substances pass from said sample to said carrier fluid, while controlling flow rates of the carrier fluid and the sample, such that a gas partial pressure of the carrier fluid exiting the countercurrent exchanger is substantially similar to a gas partial pressure of the sample entering the countercurrent exchanger;

passing the carrier exiting the countercurrent exchanger through a tubular direct insertion membrane probe (t-DIMP) to remove gases and other volatile substances from the carrier fluid after exiting the countercurrent exchanger; and measuring said partial pressures of said gases and volatile substances removed from said carrier fluid using a mass spectrometer.

18. A method as in claim 17, wherein said equilibrating step comprises the step of inducing secondary flows between said liquid and said carrier fluid when said liquid and said carrier fluid are passed in opposing directions along respective sides of a membrane.

19. A method as in claim 17, wherein said equilibrating step comprises the step of passing said liquid and said carrier fluid in opposing directions through respective complementary spiral channels separated by a membrane so as to permit said gases and volatile substances to pass from said liquid through said membrane to said carrier liquid.

20. A method for determining the partial pressures of gases and other volatile substances dissolved in a liquid in a manner which is substantially independent of the solubility of said gases and other volatile substances in said liquid, comprising the steps of:

equilibrating a carrier fluid with a sample of said liquid using a countercurrent exchanger through which said gases and other volatile substances pass from said sample to said carrier fluid, such that a gas partial pressure of the carrier fluid exiting the countercurrent exchanger is substantially similar to a gas partial pressure of the sample entering the countercurrent exchanger;

passing said equilibrated carrier fluid through a tubular direct insertion membrane probe (t-DIMP) to remove said gases and other volatile substances from the equilibrated carrier fluid; and measuring said partial pressures of said gases and volatile substances removed from the equilibrated carrier fluid, wherein flow rates of the carrier fluid and the sample of liquid are controlled during the equilibrating step.

21. A method as in claim 20, wherein said equilibrating step comprises the step of inducing secondary flows between said liquid and said carrier fluid when said liquid and said carrier fluid are passed in opposing directions along respective sides of a membrane.

* * * * *